US009658133B2

United States Patent
Kakimoto et al.

(10) Patent No.: US 9,658,133 B2
(45) Date of Patent: May 23, 2017

(54) MULTIGAS SENSOR AND MULTIGAS SENSOR DEVICE

(71) Applicant: NGK SPARK PLUG CO., LTD., Nagoya-shi, Aichi (JP)

(72) Inventors: Shiro Kakimoto, Kasugai (JP); Yoshihiro Nakano, Komaki (JP); Tetsuo Yamada, Komaki (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 143 days.

(21) Appl. No.: 14/325,961

(22) Filed: Jul. 8, 2014

(65) Prior Publication Data

US 2015/0013431 A1 Jan. 15, 2015

(30) Foreign Application Priority Data

Jul. 9, 2013 (JP) ................................ 2013-143263
May 28, 2014 (JP) ................................ 2014-109777

(51) Int. Cl.
*G01N 7/00* (2006.01)
*G01M 15/10* (2006.01)
(Continued)

(52) U.S. Cl.
CPC ......... *G01M 15/104* (2013.01); *F01N 11/007* (2013.01); *G01N 27/419* (2013.01);
(Continued)

(58) Field of Classification Search
CPC .............. G01M 15/102; G01M 15/104; G01N 15/0656; G01N 1/2252; F01N 2560/05; F01N 11/007; Y02T 10/47
(Continued)

(56) References Cited

U.S. PATENT DOCUMENTS

2005/0241937 A1* 11/2005 Shichida ............ G01N 27/4077
204/424
2007/0243760 A1* 10/2007 Fujita ................. G01N 27/4071
439/585
(Continued)

FOREIGN PATENT DOCUMENTS

JP  2001-133447 A  5/2001
JP  2010-38806 A   2/2010
(Continued)

OTHER PUBLICATIONS

Communication dated Jul. 25, 2016, issued by the Japanese Patent Office in counterpart Japanese application No. 2014-109777.

*Primary Examiner* — Eric S McCall
*Assistant Examiner* — Mohammed E Keramet-Amircolai
(74) *Attorney, Agent, or Firm* — Sughrue Mion, PLLC

(57) ABSTRACT

A multigas sensor (200A) includes a multigas sensor element portion (100A) having: a $NO_x$ sensor portion (30A) which detects the concentration of $NO_x$; and first and second ammonia sensor portions (42x, 42y) having different ratios between a sensitivity of ammonia and a sensitivity of $NO_x$. The multigas sensor element portion has a plate-like shape which extends in the direction of the axis O. A temperature detecting portion (6) used for controlling the temperature of the $NO_x$ sensor portion is disposed in the multigas sensor element portion. The first and second ammonia sensor portions are disposed on the outer surface of the $NO_x$ sensor portion so that at least parts of the first and second ammonia sensor portions overlap with a first region (6s) which is defined in the width direction by ends in the axial direction of the temperature detecting portion.

11 Claims, 8 Drawing Sheets

(51) Int. Cl.
*F01N 11/00* (2006.01)
*G01N 27/419* (2006.01)
*G01N 33/00* (2006.01)

(52) U.S. Cl.
CPC .. *F01N 2560/021* (2013.01); *F01N 2560/026* (2013.01); *G01N 33/0037* (2013.01); *G01N 33/0054* (2013.01)

(58) Field of Classification Search
USPC ........................................ 73/23.31
See application file for complete search history.

(56) References Cited

U.S. PATENT DOCUMENTS

| | | | |
|---|---|---|---|
| 2007/0251823 A1* | 11/2007 | Yamada | G01N 27/4077 204/424 |
| 2008/0067066 A1* | 3/2008 | Okumura | G01N 27/4077 204/424 |
| 2008/0073209 A1* | 3/2008 | Yamada | G01N 27/4071 204/424 |
| 2009/0211906 A1* | 8/2009 | Sugaya | G01N 27/4075 204/424 |
| 2009/0242426 A1 | 10/2009 | Kilinc et al. | |
| 2010/0161242 A1 | 6/2010 | Wang et al. | |
| 2011/0048970 A1* | 3/2011 | Sugaya | G01N 27/419 205/781 |
| 2012/0145543 A1 | 6/2012 | Sugaya et al. | |
| 2013/0063619 A1 | 3/2013 | Asai | |

FOREIGN PATENT DOCUMENTS

| | | | | |
|---|---|---|---|---|
| JP | 2011-75546 A | 4/2011 | | |
| JP | EP 2463648 A2 * | 6/2012 | ......... | G01N 27/4074 |
| JP | 2012-127668 A | 7/2012 | | |
| JP | 2013-221931 A | 10/2013 | | |
| JP | 2014-215116 A | 11/2014 | | |

* cited by examiner

MULTIGAS SENSOR AND MULTIGAS SENSOR DEVICE

BACKGROUND OF THE INVENTION

1. Field of the Invention

The present invention relates to a multigas sensor and multigas sensor device used for measuring the concentrations of nitrogen oxide and ammonia contained in a gas to be measured.

2. Description of the Related Art

As a technique for purifying nitrogen oxide ($NO_x$) contained in an exhaust gas discharged from an internal combustion engine such as a diesel engine, recently, a urea SCR (Selective Catalytic Reduction) system has attracted attention. In the urea SCR system, ammonia ($NH_3$) and nitrogen oxide ($NO_x$) chemically react with each other so as to reduce the nitrogen oxide to nitrogen ($N_2$), thereby purifying nitrogen oxide contained in an exhaust gas.

In the urea SCR system, there is a possibility that, when the amount of ammonia supplied to nitrogen oxide is excessive, unreacted ammonia which remains contained in the exhaust gas is discharged to the outside. In order to suppress such discharge of unreacted ammonia, a multigas sensor which includes a sensor element for measuring the concentration of ammonia contained in an exhaust gas, and which can measure the concentrations of a plurality of kinds of gasses is used in a urea SCR system (for example, see JP 2011-075546A (Patent Document 1) and US 2010/0161242A (Patent Document 2)). In the urea SCR system, the amount of ammonia to be used in the reduction of nitrogen oxide is adjusted so that the concentration of ammonia to be measured in the multigas sensor, i.e., that of ammonia contained in the exhaust gas, is within a predetermined range.

3. Problems to be Solved by the Invention

The multigas sensor disclosed in Patent Document 1 is configured by disposing an $NH_3$ sensing cell in a $NO_x$ sensor. In the multigas sensor, it is possible to obtain only measurement signals which are output from the $NO_x$ sensor and the $NH_3$ sensing cell, respectively. In the case where three kinds of gases such as nitrogen monoxide (NO), nitrogen dioxide ($NO_2$), and ammonia ($NH_3$) are to be measured, therefore, it is difficult to correctly calculate the concentrations of the three kinds of gases, and there is a possibility that only concentrations with insufficient accuracies can be obtained.

The multigas sensor disclosed in Patent Document 2 is configured by combining together an $NH_3$ sensing cell, a $NO_2$ sensing cell, and a $NO_x$ cell. The multigas sensor calculates the concentrations of ammonia, nitrogen monoxide, and nitrogen dioxide, respectively based on measurement signals of the $NH_3$ sensing cell, the $NO_2$ sensing cell, and the $NO_x$ cell.

In the multigas sensor disclosed in Patent Document 2, however, the electrodes of the $NH_3$ sensing cell and the $NO_2$ sensing cell are formed by different materials. Therefore, it is necessary to take a countermeasure for ensuring the reliability of both the $NH_3$ sensing cell and the $NO_2$ sensing cell. Namely, the electrodes may deteriorate in different degrees. When the use period of the multigas sensor is long, therefore, a problem arises in that the deterioration degree of the electrodes largely differ from each other, and the accuracy of the measurement of the concentration of a certain gas species is impaired.

SUMMARY OF THE INVENTION

The present invention has been made in order to solve the above-discussed problems. It is therefore an object of the invention to provide a multigas sensor and multigas sensor device which maintains good measurement accuracy of $NO_x$ and ammonia concentrations.

The above object has been achieved by providing (1) a multigas sensor which comprises a multigas sensor element portion including: a $NO_x$ sensor portion which detects a concentration of $NO_x$ in a gas to be measured; and two ammonia sensor portions which detect a concentration of ammonia in the gas to be measured, the sensor portions being first and second ammonia sensor portions having different ratios between a sensitivity of ammonia and a sensitivity of $NO_x$, wherein the multigas sensor element portion has a plate shape which extends in an axial direction, a temperature detecting portion which controls a temperature of the $NO_x$ sensor portion is disposed in the multigas sensor element portion, and the first and second ammonia sensor portions are disposed on an outer surface of the $NO_x$ sensor portion, at least parts of the first and second ammonia sensor portions overlapping with a first region of the multigas sensor element portion, the first region being defined in a width direction by ends in the axial direction of the temperature detecting portion.

According to the multigas sensor (1), the first and second ammonia sensor portions have different ratios between a sensitivity of ammonia and a sensitivity of $NO_x$, and, in measurement, outputs of different values can therefore be obtained from the $NO_x$ sensor portion and the first and second ammonia sensor portions, respectively. When calculations are performed using the three outputs, the concentrations of $NO_x$ and ammonia can be obtained.

Moreover, the first and second ammonia sensor portions are disposed on the outer surface of the $NO_x$ sensor portion so that at least parts of the portions overlap with the first region of the multigas sensor element portion, the first region being defined in the width direction by the ends in the axial direction of the temperature detecting portion. The temperature control of the multigas sensor element portion is performed with reference to the temperature detecting portion. In the vicinity of the temperature detecting portion, therefore, the temperature of the multigas sensor element portion is maintained at a most stable value (a value from which the temperature can be estimated). The first and second ammonia sensor portions are placed in the first region which is in the vicinity of the temperature detecting portion. Consequently, the temperatures of the ammonia sensor portions can be maintained at a stable value, and hence the temperature dependency of the sensitivity ratios themselves can be reduced.

In a preferred embodiment (2) of the multigas sensor of (1) above, all parts of the first and second ammonia sensor portions overlap the first region.

According to the multigas sensor (2), all parts of the first and second ammonia sensor portions are included in the first region. Therefore, all parts of the first and second ammonia sensor portions can surely be positioned in proximity to the temperature detecting portion, and the temperature dependency of the sensitivity ratios can be further reduced.

In another preferred embodiment (3) of the multigas sensor of (1) or (2) above, the temperature detecting portion is positioned in a middle portion in the width direction of the multigas sensor element portion, and the first and second ammonia sensor portions are disposed on both sides in the width direction of the first region across a second region which is defined in the axial direction by ends in the width direction of the temperature detecting portion.

According to the multigas sensor (3), the ammonia sensor portions are disposed so as to interpose in the width direction the second region where the temperature detecting portion is disposed, and therefore both ammonia sensor portions are positioned adjacent to the temperature detecting portion. As a result, as compared with the case where the ammonia sensor portions are placed on one side of the temperature detecting portion, and only one of the ammonia sensor portions is adjacent to the temperature detecting portion, the temperature difference between the first and second ammonia sensor portions can be suppressed, and the temperature dependency of the sensitivity ratios can be further reduced.

In yet another preferred embodiment (4) of the multigas sensor (3) above, the first and second ammonia sensor portions are positioned so as to be shifted away from the second region.

According to the multigas sensor (4), the first and second ammonia sensor portions are separated from the second region in the width direction, and hence the distances between the ammonia sensor portions and the second region can be made substantially equal to each other. Therefore, the temperature difference between the first and second ammonia sensor portions can be suppressed, and the temperature dependency of the sensitivity ratios can be further reduced.

In yet another preferred embodiment (5) of the multigas sensor of any of (1) to (4) above, the $NO_x$ sensor portion is configured by stacking a $NO_x$ sensing portion in which the temperature detecting portion is disposed and a heater for heating the $NO_x$ sensing portion, and the first and second ammonia sensor portions are disposed on an outer surface of the $NO_x$ sensor portion on a side of the heater in a stacking direction of the multigas sensor element portion.

According to the multigas sensor (5), the $NO_x$ sensing portion and the first and second ammonia sensor portions are disposed so as to sandwich the heater in the stacking direction. Therefore, all of the $NO_x$ sensing portion and the first and second ammonia sensor portions are adjacent to the heater (namely, separated from the heater by a substantially same distance). As a result, as compared with the case where the $NO_x$ sensing portion and the ammonia sensor portions are placed on one side of the heater in the stacking direction, the control temperature of the temperature detecting portion which is separated by a substantially same distance from the heater functioning as a heat source is accurately reflected also in the ammonia sensor portions, and the temperatures of the ammonia sensor portions can be controlled more accurately.

In yet another preferred embodiment (6) of the multigas sensor of any of (1) to (5) above, the $NO_x$ sensor portion is configured by stacking a $NO_x$ sensing portion in which the temperature detecting portion is disposed and a heater for heating the $NO_x$ sensing portion, the heater having a heating portion on a front end side thereof in the axial direction and a pair of lead portions that extends from the heating portion toward a rear end in the axial direction, and the first and second ammonia sensor portions may at least partly overlap with each other in the axial direction in the first region.

In the case where the heater has the heating portion and the lead portions in the axial direction, the heater generates heat unevenly in the axial direction. In the configuration where the first and second ammonia sensor portions at least partly overlap each other in the axial direction in the first region, the ammonia sensor portions in the overlapping area are heated evenly in the axial direction by the heater. Therefore, the temperature dependency of the sensitivity ratios can be further reduced.

In yet another preferred embodiment (7) of the multigas sensor of (6) above, all parts of one of the first and second ammonia sensor portions overlap with another one of the first and second ammonia sensor portions in the axial direction in the first region.

According to the multigas sensor (7), in the case where the heater generates heat unevenly in the axial direction as described above, one of the ammonia sensor portions completely overlaps the other ammonia sensor portion in the axial direction (located inside the other ammonia sensor portion, or the ammonia sensor portions coincide with each other in the axial direction). Also, in the overlapping area, the ammonia sensor portions are heated more evenly in the axial direction by the heater. Therefore, the temperature dependency of the sensitivity ratios can still be further reduced.

In yet another preferred embodiment (8) of the multigas sensor of any of (6) or (7) above, each of the first and second ammonia sensor portions includes a solid electrolyte body and a pair of electrodes which are disposed respectively on opposing surfaces of the solid electrolyte body, and one of the paired electrodes is disposed on the outer surface of the $NO_x$ sensor portion.

According to the multigas sensor (8), as compared with the case where pairs of electrodes are disposed on one surface of a solid electrolyte body, the plan dimensions of the solid electrolyte body, and therefore the dimensions of the first and second ammonia sensor portions, can be reduced. When the ammonia sensor portions are miniaturized, the above-mentioned placement structure can be easily realized, and the uneven temperature distribution due to the positions of the ammonia sensor portions can be reduced. As a result, the temperature dependency of the sensitivity ratios can be further reduced.

In yet another preferred embodiment (9) of the multigas sensor of any of (1) to (8) above, axial lengths of the first and second ammonia sensor portions are shorter than an axial length of the first region.

According to the multigas sensor (9), the dimensions of the first and second ammonia sensor portions in the axial direction can be further reduced, and the sensor can be miniaturized. Moreover, the uneven temperature distribution of the ammonia sensor portions in the axial direction can be reduced, and the temperature dependency of the sensitivity ratios can be further reduced.

In yet another preferred embodiment (10) of the multigas sensor of any of (1) to (9) above, a protective layer which covers the first and second ammonia sensor portions is disposed in the multigas sensor, and the protective layer integrally covers both the first and second ammonia sensor portions.

According to the multigas sensor (10), the common protective layer is used, thereby allowing the protective layer covering the first and second ammonia sensor portions to have a constant porosity (gas permeability). Therefore, the gas to be measured is introduced in the ammonia sensor portions at the same rate, and hence it is possible to suppress deviation of the sensitivity ratios of the ammonia sensor portions due to the protective layer.

In a second aspect (11), the invention provides a multigas sensor device comprising: the multigas sensor of (1) above, and a calculating portion which calculates concentrations of nitrogen monoxide, nitrogen dioxide, and ammonia contained in the gas to be measured, based on outputs of the $NO_x$ sensor portion and the first and second ammonia sensor portions.

The multigas sensor (1) is disposed in the multigas sensor device (11). Therefore, calculations can be performed based on outputs of different values from the $NO_x$ sensor portion and the first and second ammonia sensor portions, to output the concentrations of $NO_x$ and ammonia.

Advantageous Effects of Invention

According to the invention, in a measurement by the multigas sensor, good measurement accuracy of $NO_X$ and ammonia concentrations can be maintained.

DESCRIPTION OF REFERENCE SYMBOLS

Figure 1:
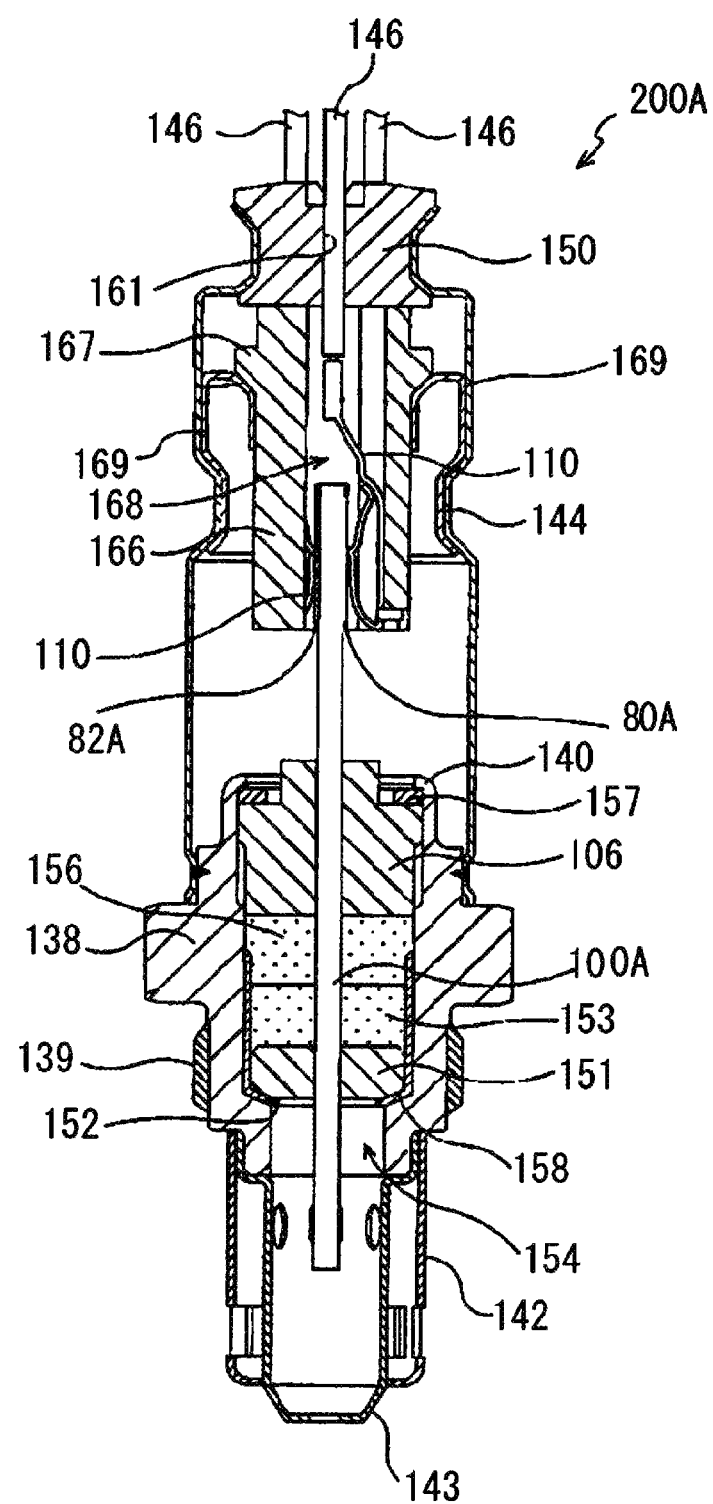
FIG. 1 is a sectional view of a multigas sensor taken along the longitudinal direction.

Reference symbols used to identify various features in the drawings include the following.
6 temperature detecting portion (oxygen concentration detection cell)
6s first region
6x second region
21 heating resistor
23g protective layer
30A $NO_x$ sensor portion
42x to 42x6 first ammonia sensor portion
42y to 42y6 second ammonia sensor portion
42dx, 42dx1, 42dy, 42dy1 solid electrolyte body
60 calculating portion (microcomputer)
100A, 100A1 multigas sensor element portion
200A multigas sensor
400, 402 multigas sensor device
O axial direction

DESCRIPTION OF THE PREFERRED EMBODIMENTS

Hereinafter, an embodiment of the invention will be described with reference to FIGS. 1 to 3. However, the present invention should not be construed as being limited thereto.

Figure 2:
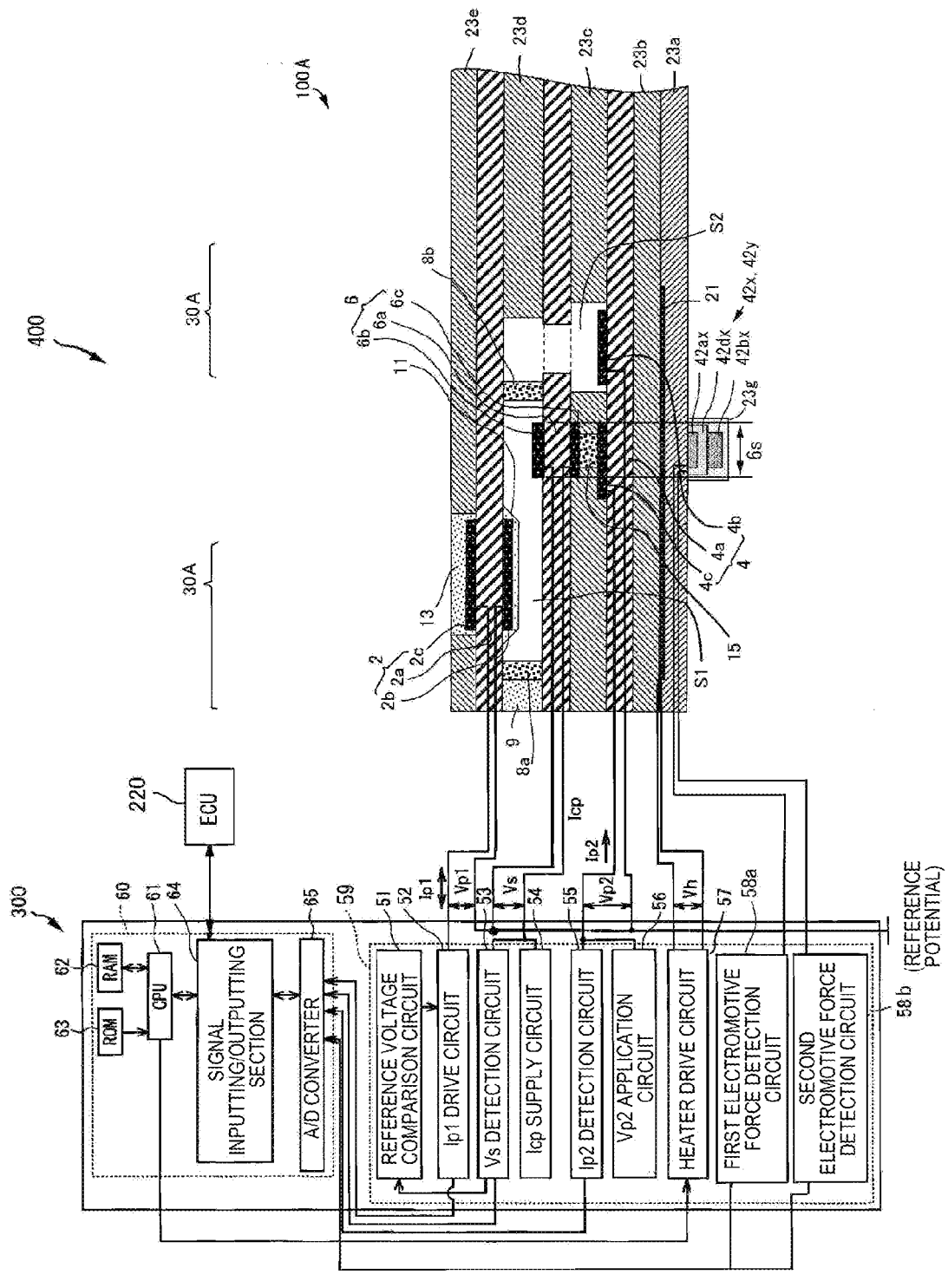
FIG. 2 is a block diagram showing the configurations of the multigas sensor and a gas sensor controller.
Figure 3:
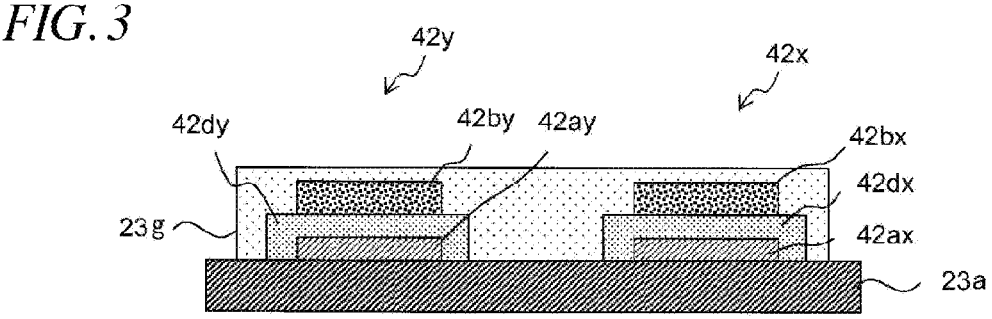
FIG. 3 is a sectional view showing the configurations of first and second ammonia sensor portions.

FIG. 1 is a sectional view of a multigas sensor taken along the longitudinal direction, FIG. 2 is a block diagram showing the configurations of a multigas sensor device, and FIG. 3 is a sectional view showing the configurations of first and second ammonia sensor portions.

The multigas sensor device 400 of the embodiment is to be used in a urea SCR system which purifies nitrogen oxide ($NO_X$) contained in an exhaust gas (gas to be measured) discharged from a diesel engine. More specifically, the device measures the concentrations of nitrogen monoxide (NO), nitrogen dioxide ($NO_2$), and ammonia contained in an exhaust gas in which $NO_X$ and ammonia (urea) contained in the exhaust gas have reacted with each other.

An engine to which the multigas sensor device 400 of the embodiment is to be applied may be a diesel engine described above, or a gasoline engine. The type of engine to which the embodiment is applicable is not particularly limited.

As shown in FIG. 1, the multigas sensor 200A is an assembly into which a multigas sensor element portion 100A for detecting the ammonia concentration and the $NO_x$ concentration is incorporated. The multigas sensor 200A includes: the plate-like multigas sensor element portion 100A extending in the axial direction; a tubular metal shell 138 in which a threaded portion 139 adapted to be fixed to an exhaust pipe is formed on the outer surface; a tubular ceramic sleeve 106 which is placed so as to radially surround the multigas sensor element portion 100A; an insulation contact member 166 which has a contact insertion hole 168 extending therethrough in the axial direction, and which is placed so that the inner wall surface of the contact insertion hole 168 surrounds the circumference of a rear end portion of the multigas sensor element portion 100A; and a plurality of connection terminals 110 (in FIG. 1, only two terminals are shown) placed between the multigas sensor element portion 100A and the insulation contact member 166.

The metal shell 138 is configured into a substantially tubular shape having a through hole 154 extending therethrough in the axial direction, and a ledge 152 projecting radially inward in the through hole 154. The metallic shell 138 holds the multigas sensor element portion 100A in the through hole 154 in a state where the front end side of the multigas sensor element portion 100A is placed outside the front end side of the through hole 154, and electrode terminal portions 80A, 82A are placed outside the rear end side of the through hole 154. Furthermore, the ledge 152 is formed as a radially inward tapered surface which is inclined with respect to a plane perpendicular to the axial direction.

An annular ceramic holder 151, powder filler layers 153, 156 (hereinafter, also referred to as the talc rings 153, 156), and the above-mentioned ceramic sleeve 106 are stacked in this order from the front side to the rear side in the through hole 154 of the metal shell 138 in a state where they radially surround the multigas sensor element portion 100A. A crimp packing 157 is disposed between the ceramic sleeve 106 and a rear end portion 140 of the metallic shell 138. A metal holder 158 is disposed between the ceramic holder 151 and the ledge 152 of the metal shell 138 to hold the talc ring 153 and the ceramic holder 151. The rear end portion 140 of the metal shell 138 is crimped so as to press the ceramic sleeve 106 toward the front end side, via the crimp packing 157.

Double external and internal protectors 142, 143 which are made of metal (for example, stainless steel), which cover the projection portion of the multigas sensor element portion 100A, and which have a plurality of holes are attached by welding or the like to the outer circumference of the front end side (in FIG. 1, lower portion) of the metallic shell 138.

An external cylinder 144 is fixed to the outer circumference of the rear end side of the metal shell 138. A grommet 150 is disposed in an opening of a rear end side (in FIG. 1, an upper portion) of the external cylinder 144. In the grommet 150, a lead-wire through hole 161 is formed through which a plurality of lead wires 146 (in FIG. 1, only three lead wires are shown) electrically connected respectively to the electrode terminal portions 80A, 82A of the multigas sensor element portion 100A are passed. In FIG. 1, for purposes of simplification, the electrode terminal portions on the front and back surfaces of the multigas sensor element portion 100A are represented by the reference numerals 80A, 82A. In actuality, a plurality of electrode terminal portions are formed according to the number of electrodes and the like of a $NO_x$ sensor portion 30A and first and second ammonia sensor portions 42$x$, 42$y$ which are described below.

An insulation contact member 166 is placed on the side of the rear end (in FIG. 1, the upper side) of the multigas sensor element portion 100A which projects from the rear end portion 140 of the metal shell 138. The insulation contact member 166 is disposed around the electrode terminal portions 80A, 82A formed on the front and back surfaces of the rear end side of the multigas sensor element portion 100A. The insulation contact member 166 is formed into a tubular shape having the contact insertion hole 168 which is passed therethrough in the axial direction. The insulation contact member 166 has a flange portion 167 projecting radially outward from the outer surface of the insulation contact member 166. The insulation contact member 166 is caused to be disposed in the external cylinder 144 by the flange portion 167 which butts against the external cylinder 144 via a holding member 169. The connection terminals 110 on the side of the insulation contact member 166 are electrically connected with the electrode terminal portions 80A, 82A of the multigas sensor element portion 100A, thereby establishing electrical communication with the outside via the lead wires 146.

FIG. 2 is a block diagram showing a configuration of the multigas sensor device 400 of the embodiment of the invention. For convenience in description, FIG. 2 shows only the longitudinal section of the multigas sensor element portion 100A which is accommodated in the multigas sensor 200A.

The multigas sensor device 400 includes a controller 300 and the multigas sensor 200A (multigas sensor element portion 100A) which is connected thereto. The controller 300 is mounted in an unillustrated vehicle including an internal combustion engine (engine). The controller 300 is electrically connected to an ECU 220. Ends of the lead wires 146 extending from the multigas sensor 200A are connected to respective connectors which in turn are electrically connected to corresponding connectors of the controller 300.

Next, the configuration of the multigas sensor element portion 100A will be described. The multigas sensor element portion 100A includes the $NO_x$ sensor portion 30A having a configuration which is similar to that of a known $NO_x$ sensor, and the first and second ammonia sensor portions 42$x$, 42$y$ which are two ammonia sensor portions. As described in detail below, the first and second ammonia sensor portions 42$x$, 42$y$ are formed on the outer surface of the $NO_x$ sensor portion 30A.

First, the $NO_x$ sensor portion 30A has a structure in which an insulation layer 23$e$, a first solid electrolyte body 2$a$, an insulation layer 23$d$, a third solid electrolyte body 6$a$, an insulation layer 23$c$, a second solid electrolyte body 4$a$, and insulation layers 23$b$, 23$a$ are stacked together in this order. A first measuring chamber S1 is defined between the first solid electrolyte body 2$a$ and the third solid electrolyte body 6$a$. An exhaust gas is introduced from the outside into the first measuring chamber S1 through a first diffusion resistor 8$a$ which is arranged in the left end (inlet) of the first measuring chamber S1. A protective layer 9 formed by a porous material is arranged outside the first diffusion resistor 8$a$.

A second diffusion resistor 8$b$ is arranged at the end of the first measuring chamber S1 opposite to the inlet. A second measuring chamber (corresponding to "$NO_x$ measuring chamber" in the invention) S2 which communicates with the first measuring chamber S1 is defined on the right side of the first measuring chamber S1 through the second diffusion resistor 8$b$. The second measuring chamber S2 is formed between the first solid electrolyte body 2$a$ and the second solid electrolyte body 4$a$ while passing through the third solid electrolyte body 6$a$.

An elongated plate-like heating resistor 21 which extends in the longitudinal direction of the multigas sensor element portion 100A is embedded between the insulation layers 23$b$, 23$a$. In the heating resistor 21, a heating portion is disposed on the front end side in the axial direction (longitudinal direction), and a pair of lead portions are disposed so as to extend from the heating member toward the rear end side in the axial direction. The heating resistor 21 and the insulation layers 23$b$, 23$a$ correspond to the "heater" of the invention. The heater is used for heating the gas sensor to an activation temperature, thereby enhancing the oxygen ion conductivities of the solid electrolyte bodies and to thereby stabilize the operation.

The insulation layers 23$a$ to 23$e$ mainly contain alumina. The first diffusion resistors 8$a$ and the second diffusion resistor 8$b$ are made of a porous substance such as alumina. The heating resistor 21 is formed of platinum or the like. The heating portion of the heating resistor 21 is formed into, for example, a meandering pattern. The shape of the heating portion is not limited to this pattern or shape.

A first pumping cell 2 includes the first solid electrolyte body 2$a$ which mainly contains oxygen ion conductive zirconia, and inner and outer first pumping electrodes 2$b$, 2$c$ which are paired with each other, and which are placed so as to sandwich the first solid electrolyte body 2$a$. The inner first pumping electrode 2$b$ faces the first measuring chamber S1. Both the inner and outer first pumping electrodes 2$b$, 2$c$ mainly contain platinum. The surface of the inner first pumping electrode 2$b$ is covered with a protective layer 11 formed by a porous material.

A portion of the insulation layer 23$e$ which corresponds to the upper surface of the outer first pumping electrode 2$c$ is cut out. The resultant cutout space is filled with a porous body 13 so that the outer first pumping electrode 2c can communicate with the outside, thereby enabling inflow and outflow of a gas (oxygen).

An oxygen concentration detection cell 6 includes the third solid electrolyte body 6a which mainly contains zirconia, and a sensing electrode 6b and reference electrode 6c which are disposed so as to sandwich the third solid electrolyte body 6a. The sensing electrode 6b faces the first measuring chamber S1 at a position located downstream of the inner first pumping electrode 2b. Both the sensing electrode 6b and the reference electrode 6c mainly contain platinum.

A portion of the insulation layer 23c is cut out so that the reference electrode 6c which is in contact with the third solid electrolyte body 6a is disposed in the resultant cutout space, and the cutout space is filled with a porous member, thereby forming a reference oxygen chamber 15. When an Icp supply circuit 54 is used in the oxygen concentration detection cell 6, and a very weak constant current is previously supplied to the oxygen concentration detection cell 6, oxygen is transported from the first measuring chamber S1 to the reference oxygen chamber 15, thereby establishing an oxygen reference.

A second pumping cell 4 includes the second solid electrolyte body 4a which mainly contains zirconia, an inner second pumping electrode 4b which is disposed on the surface of the second solid electrolyte body 4a facing the second measuring chamber S2, and a second pumping counter electrode 4c which is paired with inner second pumping electrode 4b. Both the inner second pumping electrode 4b and the second pumping counter electrode 4c mainly contain platinum.

The second pumping counter electrode 4c is placed in the cutout space of the insulation layer 23c on the second solid electrolyte body 4a, and opposes the reference electrode 6c to face the reference oxygen chamber 15.

The inner first pumping electrode 2b, the sensing electrode 6b, and the inner second pumping electrode 4b are connected to a reference potential.

In the $NO_x$ sensor portion 30A, the portions (for example, the first pumping cell 2, the oxygen concentration detection cell 6, and the second pumping cell 4) except the heating resistor 21 and the insulation layers 23b, 23a correspond to the "$NO_x$ sensing portion" of the invention.

Next, the first and second ammonia sensor portions 42x, 42y which are two ammonia sensor portions will be described.

As shown in FIG. 3, the multigas sensor element portion 100A has the first and second ammonia sensor portions 42x, 42y which are separated from each other in the width direction. In FIG. 2, only the first ammonia sensor portion 42x is shown.

The first and second ammonia sensor portions 42x, 42y are formed on the insulation layer 23a which is the outer surface (lower surface) of the $NO_x$ sensor portion 30A. In the first ammonia sensor portion 42x, more specifically, a first reference electrode 42ax is formed on the insulation layer 23a, and a first solid electrolyte body 42dx is formed while covering the upper and side surfaces of the first reference electrode 42ax. Moreover, a first sensing electrode 42bx is formed on the surface of the first solid electrolyte body 42dx. The concentration of ammonia in the gas to be measured is detected based on a change in electromotive force generated between the first reference electrode 42ax and the first sensing electrode 42bx. In the second ammonia sensor portion 42y, similarly, a second reference electrode 42ay is formed on the insulation layer 23a, and a second solid electrolyte body 42dy is formed while covering the upper and side surfaces of the second reference electrode 42ay. Moreover, a second sensing electrode 42by is formed on the surface of the second solid electrolyte body 42dy.

In the embodiment, as described above, the $NO_x$ sensing portion and the first and second ammonia sensor portions 42x, 42y are placed so as to sandwich the heater (the heating resistor 21 and the insulation layers 23b, 23a) in the stacking direction. Therefore, all of the $NO_x$ sensing portion and the ammonia sensor portions 42x, 42y are adjacent to the heater (separated from the heater by substantially the same distance). As a result, as compared with the case where the $NO_x$ sensing portion and the ammonia sensor portions 42x, 42y are placed on one side of the heater in the stacking direction, the control temperature of the oxygen concentration detection cell 6 which is separated by substantially the same distance from the heater functioning a heat source is accurately reflected also in the ammonia sensor portions 42x, 42y, and the respective temperatures of the ammonia sensor portions 42x, 42y can be controlled more accurately.

In the embodiment, each of the first and second ammonia sensor portions 42x, 42y includes the solid electrolyte body 42dx or 42dy, and the pair of electrodes (42ax, 42bx) or (42ay, 42by) which are disposed respectively on opposing surfaces of the solid electrolyte body 42dx or 42dy. In the paired electrodes, the first reference electrode 42ax or the second reference electrode 42ay is disposed on the outer surface of the $NO_x$ sensor portion 30A. As compared with the case where a pair of electrodes are disposed on one surface of each of the solid electrolyte bodies 42dx, 42dy, the plan dimensions of the solid electrolyte body 42dx or 42dy, and therefore the dimensions of the first and second ammonia sensor portions 42x, 42y can be reduced. When the ammonia sensor portions 42x, 42y are miniaturized, the below-mentioned placement structure can be easily realized, and uneven temperature distribution due to the positions of the ammonia sensor portions 42x, 42y can be reduced. Also, between the first and second ammonia sensor portions 42x, 42y, the temperature dependency of the sensitivity ratios of ammonia to $NO_x$ can be further reduced. Thus, the concentrations of $NO_x$ and ammonia can be obtained more accurately.

In the case where the ammonia sensor portions need not be miniaturized, for example, each of the first and second ammonia sensor portions 42x, 42y may include paired electrodes on one surface of the solid electrolyte body 42dx or 42dy.

Furthermore, the first and second ammonia sensor portions 42x, 42y are integrally covered with a protective layer 23g made of a porous material.

The protective layer 23g prevents poisoning substances from adhering to the first and second ammonia sensor portions 42x, 42y, and adjusts the diffusion rate of the gas to be measured which flows from the outside into the first and second ammonia sensor portions 42x, 42y. An example of the material forming the protective layer 23g is a material selected from the group consisting of alumina (aluminum oxide), spinel ($MgAl_2O_4$), silica alumina, and mullite. The diffusion rate of the gas to be measured due to the protective layer 23g can be regulated by adjusting the thickness of the protective layer 23g, the particle size, particle size distribution, porosity, mixing ratio of the material, and the like.

When the protective layer 23g integrally covers both the first and second ammonia sensor portions 42x, 42y as shown in FIG. 3, the porosity (gas permeability) of the protective layer 23g which covers the first and second ammonia sensor portions 42x, 42y is constant. Therefore, the gas to be measured is introduced into the ammonia sensor portions at the same rate, and hence the sensitivity ratios of the first and second ammonia sensor portions 42$x$, 42$y$ do not deviate on account of having provided the protective layer 23$g$, and the concentrations of $NO_x$ and ammonia can be obtained more accurately.

The protective layer 23$g$ may be disposed as in the above-described embodiment. Alternatively, the protective layer 23$g$ need not be disposed, and the first and second ammonia sensor portions 42$x$, 42$y$ and the like may be exposed. The configuration is not particularly limited. In the case where the sensitivity ratios of the first and second ammonia sensor portions 42$x$, 42$y$ are to be adjusted by the protective layer 23$g$, protective layers may be disposed respectively on the ammonia sensor portions unlike the embodiment.

The first and second sensing electrodes 42$bx$, 42$by$ may be formed of a material which mainly contains Au (for example, 70% by mass or more). The first and second reference electrodes 42$ax$, 42$ay$ may formed of Pt alone or a material which mainly contains Pt (for example, 70% by mass or more). In the first and second sensing electrodes 42$bx$, 42$by$, ammonia gas hardly burns on their surfaces. Ammonia passes through the sensing electrode 42$bx$ (42$by$), and reacts (electrode reaction) with oxygen ions at the interface between the sensing electrode 42$bx$ (42$by$) and the reference electrode 42$ax$ (42$ay$) which is below the sensing electrode, so that the concentration of ammonia is detected.

For example, the first and second ammonia sensor portions 42$x$, 42$y$ may be made of partially stabilized zirconia (YSZ).

In the invention, the impedance of the oxygen concentration detection cell 6 (corresponding to "temperature detecting portion" of the invention) is measured, and the heater (heating resistor 21) performs a heating operation based on the measured impedance. In the vicinity of the oxygen concentration detection cell 6, therefore, the temperature of the multigas sensor element portion 100A is maintained at a most stabilized value (a value from which the temperature can be estimated). The more separated a portion is from the oxygen concentration detection cell 6 in the axial direction, the more easily the portion is affected by variation of the external temperature, and therefore the temperature of the multigas sensor element portion 100A largely changes.

From the above, when the first and second ammonia sensor portions 42$x$, 42$y$ are placed so that at least parts of the portions overlap with a first region 6$s$ which is defined in the width direction by the ends of the direction of the axis O of the oxygen concentration detection cell 6, the temperatures of the first and second ammonia sensor portions 42$x$, 42$y$ can be maintained constant within a predetermined range, and the accuracy of the ammonia measurement can be improved.

When the sensing electrode 6$b$ and the reference electrode 6$c$ are regarded as a predetermined single electrode in the plan view (see FIG. 4), the first region 6$s$ is defined (broken lines in FIG. 4) in the width direction by a front end (see FIG. 2) and a rear end (see FIG. 2)) of the predetermined single electrode in the direction of the axis O. A second region 6$x$ which will be described below is a region which is in the first region 6$s$, and which is defined in the axial direction by the ends in the width direction of the oxygen concentration detection cell 6. Specifically, the second region is a region which is defined (dash-dot-dash lines in FIG. 4) in the axial direction by the ends in the width direction of the sensing electrode 6$b$ and reference electrode 6$c$ constituting the oxygen concentration detection cell 6.

In the embodiment, the sensing electrode 6$b$ and the reference electrode 6$c$ have the same dimensions and are placed at the same position. Therefore, the first region 6$s$ is a region which is defined by the front and rear ends in the direction of the axis O of the electrodes, and the second region 6$x$ is a region which is defined by the ends in the width direction of the electrodes.

Figure 4:
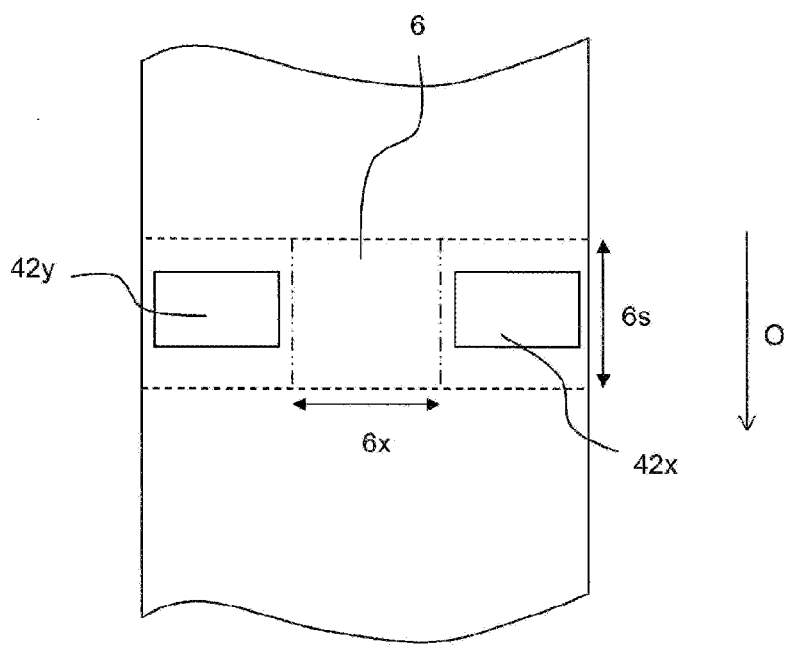
FIG. 4 is a plan view showing positional relationships of the first and second ammonia sensor portions and an oxygen concentration detecting cell.

In the case where the sensing electrode 6$b$ and reference electrode 6$c$ constituting the oxygen concentration detection cell 6 have different dimensions, or where the sensing electrode 6$b$ and the reference electrode 6$c$ are positioned so as to be shifted from each other, for example, the front and rear ends in the axial direction and ends in the width direction of the portion where the electrodes are placed can be used as the references of the boundaries of the first region 6$s$ and the second region 6$x$, when viewing the multigas sensor element portion 100A in the stacking direction (specifically, as viewed in FIG. 4).

In the sensing electrode 6$b$ and the reference electrode 6$c$, namely, the front ends of the electrodes which are disposed on the front end side in the direction of the axis O, and the rear ends of the electrodes which are placed on the rear end side of the direction of the axis O are set as the reference of the boundary of the first region, and the ends in the width direction of the electrodes which are placed in the outer side in the width direction are set as the reference of the boundary of the second region.

The ammonia sensor portions are positioned in a similar manner. In the case where, as in the embodiment, the sensing electrode and the reference electrode are formed on the surfaces of the solid electrolyte body, for example, the front and rear ends in the direction of the axis O and ends in the width direction of the portion where the electrodes are disposed are used as references of the positions of the ammonia sensor portions, as viewed in the stacking direction of the multigas sensor element portion 100A.

Also in the case where, in the ammonia sensor portions, the sensing electrode and the reference electrode are formed on one surface of the solid electrolyte body, the front and rear ends in the direction of the axis O and ends in the width direction of the portion where the electrodes are placed are used as references of the positions of the ammonia sensor portions.

In the example of FIG. 2, the positional relationships of the first and second ammonia sensor portions 42$x$, 42$y$ and the oxygen concentration detection cell 6 are as shown in FIG. 4. Namely, all parts of the first and second ammonia sensor portions 42$x$, 42$y$ overlap with the first region 6$s$ in the axial direction. The oxygen concentration detection cell 6 is placed in the middle portion in the width direction (direction perpendicular to the axial direction) of the multigas sensor element portion 100A. The first and second ammonia sensor portions 42$x$, 42$y$ are placed on both sides in the width direction across the second region 6$x$. In the first region 6$s$, moreover, all parts of one of the first and second ammonia sensor portions 42$x$, 42$y$ overlap with the other portion in the axial direction (in the example of FIG. 4, particularly, the first and second ammonia sensor portions 42$x$, 42$y$ coincide with each other in the axial direction).

In the embodiment, as described above, the first and second ammonia sensor portions 42$x$, 42$y$ are positioned on the outer surface of the $NO_x$ sensor portion 30A so that at least parts of the first and second ammonia sensor portions overlap with the first region 6$s$. The temperature control of the multigas sensor element portion 100A is performed with reference to the oxygen concentration detection cell 6. In the vicinity of the oxygen concentration detection cell 6, therefore, the temperature of the multigas sensor element portion 100A is maintained at a most stable value (value from which the temperature can be estimated). The first and second ammonia sensor portions 42x, 42y are placed in the first region 6s which is in the vicinity of the oxygen concentration detection cell 6. Consequently, the temperatures of the ammonia sensor portions 42x, 42y can be maintained at a stable value, and hence the temperature dependency of the sensitivity ratios can be reduced.

Moreover, all parts of the first and second ammonia sensor portions 42x, 42y overlap with the first region 6s. Therefore, all parts of the first and second ammonia sensor portions 42x, 42y can surely be placed in proximity to the oxygen concentration detection cell 6, and the temperature dependency of the sensitivity ratios can be further reduced.

Furthermore, the ammonia sensor portions 42x, 42y are disposed on both sides while interposing the second region 6x therebetween, and therefore both the ammonia sensor portions 42x, 42y are adjacent to the oxygen concentration detection cell 6. As a result, as compared with the case where the ammonia sensor portions 42x, 42y are placed on one side in the width direction of the oxygen concentration detection cell 6, and only one of the ammonia sensor portions is adjacent to the oxygen concentration detection cell 6, the temperature difference between the ammonia sensor portions 42x, 42y can be suppressed, and the temperature dependency of the sensitivity ratios can be further reduced.

Furthermore, the first and second ammonia sensor portions 42x, 42y are separated from the second region 6x in the width direction, and hence the distances between the ammonia sensor portions 42x, 42y and the second region can be made substantially equal to each other. Therefore, the temperature difference between the first and second ammonia sensor portions 42x, 42y can be suppressed, and the temperature dependency of the sensitivity ratios can be further reduced.

In the embodiment, since the heater (specifically, the heating resistor 21) has a heating portion and lead portions positioned in the axial direction, the heater generates heat unevenly in the axial direction. In the embodiment, therefore, the first and second ammonia sensor portions 42x, 42y at least partly overlap each other in the axial direction, and, in the overlapping area, the ammonia sensor portions 42x, 42y are heated evenly by the heater in the axial direction. Therefore, the temperature dependency of the sensitivity ratios can be further reduced. In the embodiment, particularly, the ammonia sensor portions 42x, 42y coincide (completely overlap) with each other in the axial direction, and the ammonia sensor portions are heated more evenly by the heater in the axial direction. Therefore, the temperature dependency of the sensitivity ratios can be still further reduced.

In the embodiment, moreover, the axial lengths of the first and second ammonia sensor portions 42x, 42y are shorter than the axial length of the first region 6s, and the ammonia sensor portions 42x, 42y located inside the first region 6s in the axial direction. When the dimensions of the first and second ammonia sensor portions 42x, 42y in the axial direction are reduced as described above, the sensor can be miniaturized. Moreover, the uneven temperature distributions of the ammonia sensor portions 42x, 42y in the axial direction can be reduced, and the temperature dependency of the sensitivity ratios can be further reduced.

Returning to FIG. 2, an example of the configuration of the controller (corresponding to "calculating portion" set forth in the claims) 300 will be described. The controller 300 includes a control circuit 59 which can be an analog circuit and microcomputer 60 which are mounted on a circuit board. The microcomputer 60 controls the entire controller 300 and includes a CPU (central processing unit) 61, a RAM 62, a ROM 63, a signal inputting/outputting section 64, an A/D converter 65, and a clock (not shown). The CPU executes programs stored in the ROM 63, etc.

The control circuit 59 includes a reference voltage comparison circuit 51, an Ip1 drive circuit 52, a Vs detection circuit 53, an Icp supply circuit 54, an Ip2 detection circuit 55, a Vp2 application circuit 56, a heater drive circuit 57, and first and second electromotive force detection circuits 58a, 58b which detect the electromotive forces of the first and second ammonia sensor portions 42x, 42y, respectively. These circuits will be described in detail below.

The control circuit 59 controls the $NO_x$ sensor portion 30A, detects a first pumping current Ip1 and second pumping current Ip2 which flow through the $NO_x$ sensor portion 30A, and supplies the detected current data to the microcomputer 60.

The first and second electromotive force detection circuits 58a, 58b detect ammonia concentration outputs (electromotive forces) between the paired electrodes of the first and second ammonia sensor portions 42x, 42y, and supply the detected electromotive force data to the microcomputer 60.

More specifically, the outer first pumping electrode 2c of the $NO_x$ sensor portion 30A is connected to the IP1 drive circuit 52, and the reference electrode 6c is connected in parallel to the Vs detection circuit 53 and the Icp supply circuit 54. The second pumping counter electrode 4c is connected in parallel to the Ip2 detection circuit 55 and the Vp2 application circuit 56. The heater circuit 57 outputting heater voltage Vh is connected to the heater (specifically, the heating resistor 21).

The pair of electrodes 42ax, 42bx of the first ammonia sensor portion 42x are connected to the first electromotive force detection circuit 58a. Similarly, the pair of electrodes 42ay, 42by of the second ammonia sensor portion 42y are connected to the second electromotive force detection circuit 58b.

The circuits 51 to 57 have the following functions.

The Ip1 drive circuit 52 supplies the first pumping current Ip1 between the inner first pumping electrode 2b and the outer first pumping electrode 2c, and detects the first pumping current Ip1 at this time.

The Vs detection circuit 53 detects a voltage Vs between the detection electrode 6b and the reference electrode 6c, and supplies the detection result to the reference voltage comparison circuit 51.

The reference voltage comparison circuit 51 compares a reference voltage (e.g., 425 mV) with the output (voltage Vs) of the Vs detection circuit 53, and supplies the comparison result to the Ip1 drive circuit 52. The Ip1 drive circuit 52 controls the direction and magnitude of the Ip1 current so that the voltage Vs becomes equal to the above-mentioned reference voltage, thereby adjusting the oxygen concentration in the first measuring chamber S1 to a predetermined value at which $NO_x$ is not decomposed.

The Icp supply circuit 54 supplies a very weak current Icp between the sensing electrode 6b and the reference electrode 6c so that oxygen is transported from the first measuring chamber S1 to the reference oxygen chamber 15, thereby exposing the reference electrode 6c to a predetermined reference oxygen concentration.

The Vp2 application circuit 56 applies between the inner second pumping electrode 4b and the second pumping counter electrode 4c, a fixed voltage Vp2 (e.g., 450 mV) at which a $NO_x$ gas contained in the gas to be measured is decomposed into oxygen and a N₂ gas, thereby decomposing $NO_x$ into nitrogen and oxygen.

The Ip2 detection circuit 55 detects the second pumping current Ip2 which flows to the second pumping cell 4, at the time when oxygen generated through decomposition of $NO_x$ is pumped out from the second measuring chamber S2 toward the second pumping counter electrode 4c via the second solid electrolyte body 4a.

The Ip1 drive circuit 52 supplies the detected value of the first pumping current Ip1 to the A/D converter 65. The Ip2 detection circuit 55 supplies the detected value of the second pumping current Ip2 to the A/D converter 65.

The A/D converter 65 digitizes these values, and supplies the digitized values to the CPU 61 via the signal inputting/outputting section 64.

Next, an example of control using the control circuit 59 will be described. First, upon supplying electric power from an external power supply in association with start of the engine, the heater circuit 57 activates the heater to heat the first pumping cell 2, the oxygen concentration detection cell 6, and the second pumping cell 4 to an activation temperature. The Icp supply circuit 54 supplies the very weak current Icp which flows between the sensing electrode 6b and the reference electrode 6c so as to transport oxygen from the first measuring chamber S1 into the reference oxygen chamber 15, thereby establishing an oxygen reference.

When the $NO_x$ sensor portion 30A is heated to an appropriate temperature by means of the heater, also the first and second ammonia sensor portions 42x, 42y on the $NO_x$ sensor portion 30A are heated to a desired temperature in accordance with the temperature rise.

When the cells are heated to the activation temperature, the first pumping cell 2 pumps out oxygen contained in the gas to be measured (exhaust gas) which has flowed into the first measuring chamber S1, from the inner first pumping electrode 2b toward the outer first pumping electrode 2c.

At this time, the oxygen concentration in the first measuring chamber S1 has a value corresponding to the electrode-to-electrode voltage (terminal-to-terminal voltage) Vs of the oxygen concentration detection cell 6, and therefore the Ip1 drive circuit 52 controls the first pumping current Ip1 flowing through the first pumping cell 2 so as to cause the electrode-to-electrode voltage Vs to become the above-mentioned reference voltage, whereby the oxygen concentration in the first measuring chamber S1 is adjusted to a level at which $NO_x$ is not decomposed.

The gas to be measured in which the oxygen concentration has been adjusted flows toward the second measuring chamber S2. The Vp2 application circuit 56 applies, as the electrode-to-electrode voltage (terminal-to-terminal voltage) of the second pumping cell 4, the fixed voltage Vp2 (voltage which is higher than the control voltage of the oxygen concentration detection cell 6, for example, 450 mV) at which a $NO_x$ gas contained in the gas to be measured is decomposed into oxygen and a N₂ gas, thereby decomposing $NO_x$ into nitrogen and oxygen. The second pumping current Ip2 is supplied to the second pumping cell 4 so as to pump out oxygen generated by decomposition of $NO_x$ from the second measuring chamber S2. At this time, the second pumping current Ip2 and the $NO_x$ concentration have a linear relationship with each other. When the Ip2 detection circuit 55 detects the second pumping current Ip2, therefore, the $NO_x$ concentration in the gas to be measured can be detected.

When the first electromotive force detection circuit 58a detects the ammonia concentration output (electromotive force) between the pair of electrodes 42ax, 42bx, and the second electromotive force detection circuit 58b detects the ammonia concentration output (electromotive force) between the pair of electrodes 42ay, 42by, the ammonia concentration in the gas-to-be-measured can be detected as described below.

The process in which the microcomputer 60 of the controller 300 calculates the concentrations of various gases will be described.

First, the reason why the two ammonia sensor portions or the first and second ammonia sensor portions 42x, 42y are disposed will be described. An ammonia sensor portion detects not only ammonia but also $NO_2$. When the gas to be measured contains a $NO_2$ gas in addition to ammonia, therefore, the accuracy of detection of ammonia is lowered. To address this issue, two ammonia sensor portions having different sensitivity ratios of ammonia to $NO_x$ are disposed. In this configuration, with respect to two unknown concentrations of an ammonia gas and a $NO_2$ gas, the two ammonia sensor portions detect values due to their different sensitivities, and therefore it is possible to calculate the concentrations of ammonia gas and $NO_2$. The expression sensitivity ratio of ammonia to $NO_x$ in the ammonia sensor portion" means a detection sensitivity ratio of ammonia to the total sensitivity (ammonia and $NO_x$) detected by the ammonia sensor portion. In the embodiment, the ammonia sensor portions do not detect $NO_2$ gas, and hence it is assumed that "sensitivity ratio of ammonia to $NO_x$ in the ammonia sensor portion"="sensitivity ratio of ammonia to $NO_2$ in the ammonia sensor portion". In the case where an ammonia sensor portion does not detect $NO_2$ gas, it may be assumed that "sensitivity ratio of ammonia to $NO_x$ in the ammonia sensor portion"="sensitivity ratio of ammonia to NO in the ammonia sensor portion".

The sensor output of an ammonia sensor portion is indicated by F(x, y, D) where x: concentration of ammonia, y: concentration of $NO_2$ gas, and D: concentration of $O_2$. When two $NO_2$ sensor portions having different sensitivity ratios are used, two expressions of $F_1$(mx, ny, D) and $F_2$(sx, ty, D) (where m, n, s, and t are coefficients) are obtained. In the expressions, $F_1$, $F_2$, and D are obtained from the outputs of the sensors. Therefore, two unknowns (x, y) can be solved from the two expressions. Specifically, the required calculation can be performed by eliminating y from the above two expressions, and obtaining expressions of x as indicated by Expressions (1) to (3) described below.

The sensitivity ratios to ammonia of the first and second ammonia sensor portions 42x, 42y change when the temperatures of the first and second ammonia sensor portions 42x, 42y are different from each other. As described above, therefore, the first and second ammonia sensor portions 42x, 42y are positioned so as to overlap with at least parts of the first region 6s of the oxygen concentration detection cell 6 as viewed in the axial direction, and the temperatures of the first and second ammonia sensor portions 42x, 42y are maintained constant within a predetermined range, whereby the change of the sensitivity ratio due to temperature is reduced.

Next, the detection of $NO_2$ and ammonia by the first and second ammonia sensor portions 42x, 42y, and the concentration calculations for $NO_2$ and ammonia will be described in below.

In accordance with the concentration of ammonia contained in the gas to be measured, an electromotive force is generated between the first reference electrode 42ax and first sensing electrode 42bx of the first ammonia sensor portion 42x. The first electromotive force detection circuit 58a detects the electromotive force between the first reference electrode 42ax and the first sensing electrode 42bx, as a first ammonia electromotive force. Similarly, an electromotive force according to the ammonia concentration is generated also between the second reference electrode 42ay and second sensing electrode 42by of the second ammonia sensor portion 42x, and the second electromotive force detection circuit 58a detects the electromotive force between the second reference electrode 42ay and the second sensing electrode 42by, as a second ammonia electromotive force.

The ROM 63 of the microcomputer 60 stores various data (relational expressions) which will be described below. The CPU 61 reads the various data from the ROM 63, and performs various calculation processes based on the values of the first pumping current Ip1 and the second pumping current Ip2, and the first and second ammonia electromotive forces.

Here, the ROM 63 stores "Relational expression of first ammonia electromotive force and first ammonia concentration output", "Relational expression of second ammonia electromotive force and second ammonia concentration output", "Relational expression of first pumping current Ip1 and $O_2$ concentration output", "Relational expression of second pumping current Ip2 and $NO_x$ concentration output", "Relational expression of first ammonia concentration output, second ammonia concentration output, and $O_2$ concentration output, and corrected ammonia concentration output" (Correction expression (1), refer below), "Relational expression of first ammonia concentration output, second ammonia concentration output, and $O_2$ concentration output, and corrected $NO_2$ concentration output" (Correction expression (2)), and "Relational expression of $NO_x$ concentration output, corrected ammonia concentration output, and corrected $NO_2$ concentration output, and corrected $NO_x$ concentration output" (Correction expression (3)).

The various data may be set as predetermined relational expressions as described above, or have forms which allow various gas concentrations to be calculated from the outputs of the sensors. For example, the data may be set in the form of tables, or have values (relational expressions, tables, or the like) that are obtained with using a gas model in which the gas concentration is known.

"Relational expression of first ammonia electromotive force and first ammonia concentration output" and "Relational expression of second ammonia electromotive force and second ammonia concentration output" indicate relationships between the ammonia electromotive forces which are output from the first and second ammonia sensor portions 42x, 42y, and the ammonia concentration output related to the ammonia concentration of the gas to be measured.

"Relational expression of first pumping current Ip1 and $O_2$ concentration output" indicates relationships between the first pumping current Ip1 and the $O_2$ concentration of the gas to be measured.

"Relational expression of second pumping current Ip2 and $NO_x$ concentration output" indicates relationships between the second pumping current Ip2 and the $NO_x$ concentration of the gas to be measured.

"Relational expression of first ammonia concentration output, second ammonia concentration output, and $O_2$ concentration output, and corrected ammonia concentration output" indicates relationships between the (first and second) ammonia concentration output affected by the oxygen concentration and the $NO_2$ concentration, and a corrected ammonia concentration output from which influences of the oxygen concentration and the $NO_2$ concentration are eliminated.

"Relational expression of first ammonia concentration output, second ammonia concentration output, and $O_2$ concentration output, and corrected $NO_2$ concentration output" indicates relationships between the $NO_2$ concentration output affected by the oxygen concentration and the ammonia concentration, and a corrected $NO_2$ concentration output from which influences of the oxygen concentration and the ammonia concentration are eliminated.

"Relational expression of $NO_x$ concentration output, corrected ammonia concentration output, and corrected $NO_2$ concentration output, and corrected $NO_x$ concentration output" indicates relationships between the $NO_x$ concentration output affected by the ammonia concentration and the $NO_2$ concentration, and the accurate corrected $NO_x$ concentration output from which influences of the ammonia concentration and the $NO_2$ concentration are eliminated or modified.

Next, a calculation process will be described which is performed by the CPU 61 of the microcomputer 60, and in which the $NO_x$ concentration and the ammonia concentration are obtained from the first pumping current Ip1, the second pumping current Ip2, the first electromotive force EMF, and the second ammonia electromotive force EMF.

When the first pumping current Ip1, the second pumping current Ip2, and the first and second ammonia electromotive forces are input, the CPU 61 performs the calculation process of obtaining the $O_2$ concentration output, the $NO_x$ concentration output, and the first and second ammonia concentration outputs. Specifically, "Relational expression of first ammonia electromotive force and first ammonia concentration output", "Relational expression of second ammonia electromotive force and second ammonia concentration output", "Relational expression of first pumping current Ip1 and $O_2$ concentration output", and "Relational expression of second pumping current Ip2 and $NO_x$ concentration output" are read from the ROM 63, and then the CPU performs a process of calculating the concentration outputs by using the relational expressions.

"Relational expression of first ammonia electromotive force and first ammonia concentration output" and "Relational expression of second ammonia electromotive force and second ammonia concentration output" are expressions which are set so that, in the entire EMF range which can be output by the first and second ammonia sensor portions 42x, 42y in the operating environment, the concentration of ammonia in the gas to be measured, and an ammonia concentration conversion value of the sensor have an approximately linear relationship. When conversion is performed by using such a conversion expression, calculation using changes in the inclination and the offset is enabled in the correction expressions described below.

When the $O_2$ concentration output, the $NO_x$ concentration output, and the first and second ammonia concentration outputs are obtained, the CPU performs calculations in which the correction expressions described below are used, to obtain the ammonia concentration and $NO_x$ concentration of the gas to be measured.

$$x = F(A, B, D) \qquad \text{Correction expression (1)}$$
$$= (eA - c)*(jB - h - fA + d)/$$
$$(eA - c - iB + g) + fA - d$$

$$y = F'(A, B, D) \qquad \text{Correction expression (2)}$$
$$= (jB - h - fA + d)/$$
$$(eA - c - iB + g)$$

$$z = C - ax + by \qquad \text{Correction expression (3)}$$

In the above expressions, x indicates the ammonia concentration, y indicates the $NO_2$ concentration, and z indicates the $NO_x$ concentration. Moreover, A indicates the first ammonia concentration output, B indicates the second ammonia concentration output, C indicates the $NO_x$ concentration output, and D indicates the $O_2$ concentration output. Furthermore, F and F' of the expressions (1) and (2) show that x is a function of (A, B, D). Furthermore, a and b are correction coefficients, and c, d, e, f, g, h, i, and j are coefficients which are calculated using the $O_2$ concentration output D (coefficients depending on D).

When the first ammonia concentration output (A), the second ammonia concentration output (B), the $NO_x$ concentration output (C), and the $O_2$ concentration output (D) are substituted into the above expressions (1) to (3), and then expressions are calculated, the ammonia concentration and $NO_x$ concentration of the gas to be measured are obtained.

The expressions (1) and (2) are expressions which are determined by the characteristics of the first and second ammonia sensor portions $42x$, $42y$, and the expression (3) is an expression which is determined by the characteristics of the $NO_x$ sensor portion. The expressions (1) to (3) merely show examples of correction expressions. In accordance with the gas detection characteristics, other correction expressions may be used, or the coefficients and the like may be adequately changed.

Next, actual $NH_3$ and $NO_x$ concentration outputs before and after the correction process based on the correction expressions (1) to (3) will be described.

Figure 5:
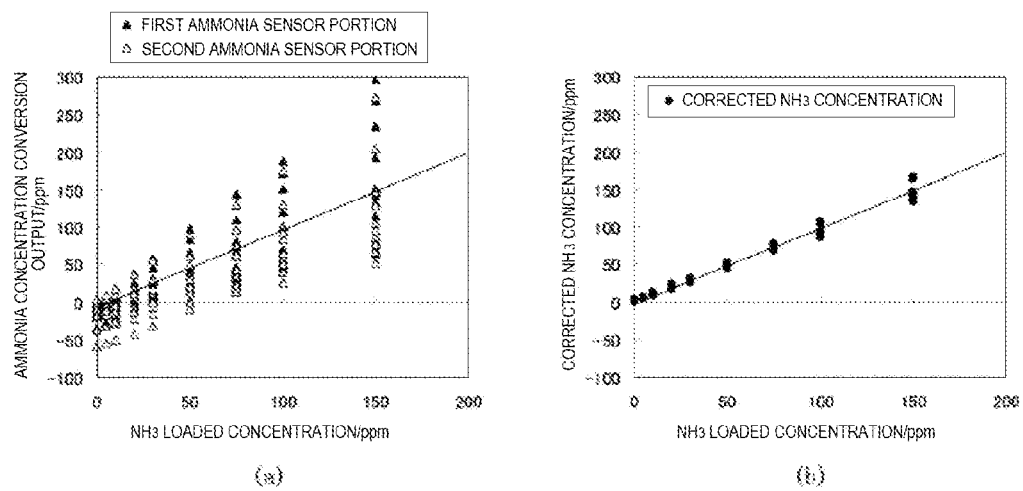
FIGS. 5A and 5B are views showing results of ammonia concentration outputs before and after performing a correction process based on correction expressions (1) to (3).

FIG. 5(a) is a graph in which ammonia concentration conversion outputs of the first and second ammonia sensor portions before the correction process in the case where 0 to 150 ppm of ammonia was loaded under conditions of $O_2=2$, 7, and 15% and $NO_2=0$, 20, 50, and 100 ppm are plotted. The concentration conversion outputs of both the first and second ammonia sensors were largely dispersed by influence of the $NO_2$ concentration and the $O_2$ concentration.

By contrast. FIG. 5(b) is a graph in which corrected ammonia concentration outputs that were obtained by substituting the values of the ammonia concentration output and the $O_2$ concentration output into the correction expression (1) are plotted with respect to the loaded concentration of ammonia. It is seen that the influence of $NO_2$ and $O_2$ can be eliminated and the ammonia concentration can be correctly calculated.

Figure 6:
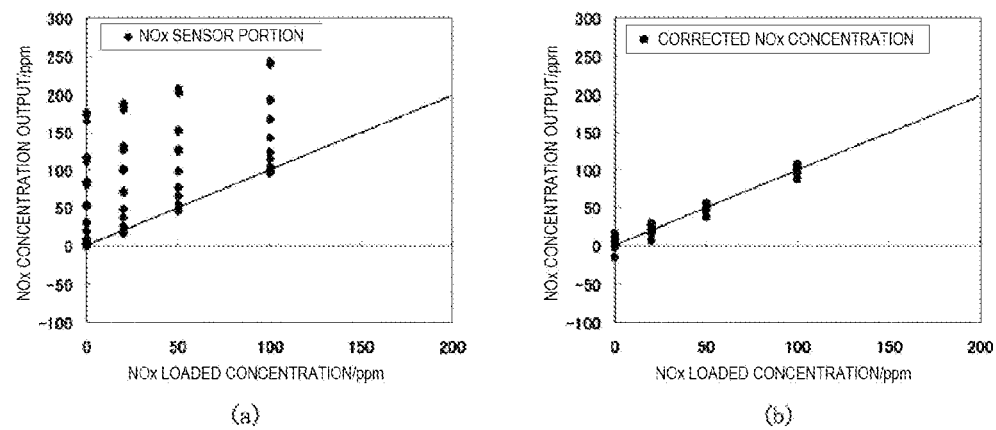
FIGS. 6A and 6B are views showing results of $NO_x$ concentration outputs before and after performing the correction process based on correction expressions (1) to (3).

Similar to FIG. 5(a), FIG. 6(a) is a graph in which $NO_x$ concentration conversion outputs of the $NO_x$ sensor portion before the correction process in the case where 0 to 100 ppm of $NO_2$ was loaded under coexistence conditions of $O_2=2$, 7, and 15% and $NH_3=0$ to 150 ppm are plotted. The $NO_x$ sensor detects also ammonia, and therefore cannot correctly detect the $NO_x$ concentration. By contrast, FIG. 6(b) is a graph in which corrected $NO_x$ concentrations that were obtained by substituting the values of the corrected ammonia concentration output, the corrected $NO_2$ concentration output, and the $NO_x$ concentration output into the correction expression (3) are plotted with respect to the loaded concentration of $NO_x$. From this, it is seen that the correct $NO_x$ concentration in which the influence of ammonia is eliminated can be calculated.

Figure 7:
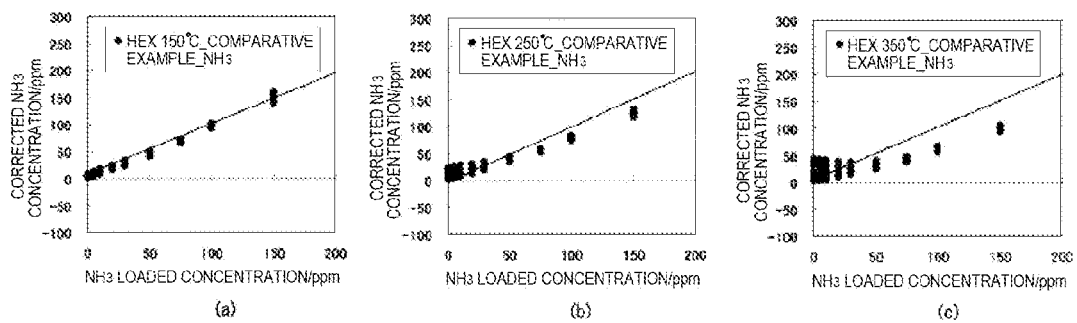
FIGS. 7A to 7C are views showing results of corrected ammonia concentration outputs depending on a change of the external temperature in the case where the second ammonia sensor portion is disposed so as not to overlap with the oxygen concentration detecting cell.
Figure 8:
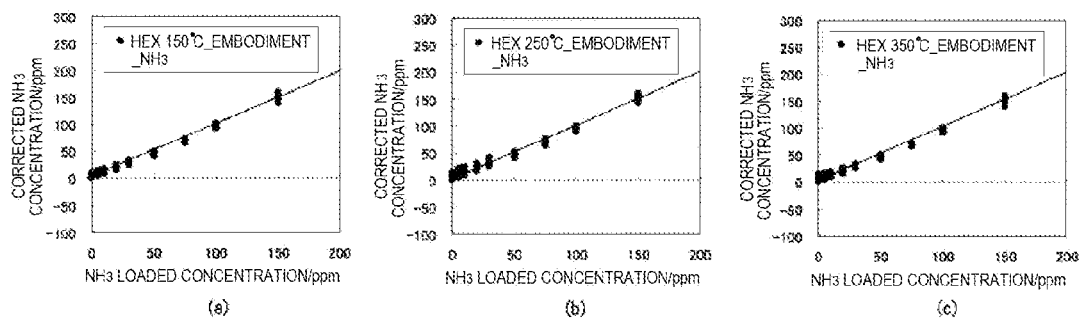
FIGS. 8A to 8C are views showing results of corrected ammonia concentration outputs depending on a change of the external temperature in the case where the first and second ammonia sensor portions are disposed so as to overlap with the oxygen concentration detecting cell.

FIGS. 7(a) to 7(c) indicate comparative examples which show the influence on the corrected ammonia concentration output due to a change of the external temperature (temperature of the multigas sensor) in the case where the second ammonia sensor portion $42y$ of the multigas sensor element portion 100A is positioned so as not to overlap with the first region $6s$ of the oxygen concentration detection cell 6. In FIGS. 7(a) to 7(c) and FIGS. 8(a) to 8(c), the temperature of "HEX" indicates the temperature of the metal shell 138, i.e., the external temperature (temperature of the multigas sensor 200A), and a change of the HEX temperature indicates a change in the external temperature. In the experiment, the corrected ammonia concentration was calculated based on the sensor outputs which were obtained by loading 0 to 150 ppm of ammonia under conditions of $O_2=2$, 7, and 15% and $NO_2=0$, 20, 50, and 100 ppm.

As shown in FIGS. 7(a) to 7(c), when one of the first and second ammonia sensor portions $42x$, $42y$ is positioned so as not to overlap with the first region $6s$ of the oxygen concentration detection cell 6, the corrected ammonia concentration output is shifted and non-proportional to the loading concentration of ammonia by variation of the external temperature (HEX temperature), and the accuracy of the measurement of the ammonia concentration is lowered. It is considered that this is caused by a phenomenon in which the temperature of the second ammonia sensor portion $42y$ is changed by the deviation of the second ammonia sensor portion $42y$ from the first region $6s$, and also the EMF output is changed.

In the case of the invention (embodiment) in which both the first and second ammonia sensor portions $42x$, $42y$ are positioned so as to overlap with at least parts of the first region $6s$, even when the external temperature (HEX temperature) is varied similar to FIGS. 7(a) to 7(c), by contrast, the corrected ammonia concentration output was substantially proportional to the loading concentration of ammonia, and the ammonia concentration was accurately measured. It is considered that this is caused by a phenomenon in which, since the first and second ammonia sensor portions $42x$, $42y$ are positioned in the vicinity of the first region $6s$, the temperatures of the sensor portions are maintained at a stable value, and the EMF output is not largely changed by variation of the external temperature.

In the invention, namely, ammonia and $NO_x$ are separately detected by differentiating the sensitivity ratios to ammonia, and therefore it is necessary to reduce as far as possible the temperature dependency of the sensitivity ratios themselves.

When the multigas sensor 200A and correction method of the embodiment of the invention are employed, therefore, ammonia and $NO_x$ can be accurately detected in a separate manner even in an environment where ammonia and $NO_x$ coexist and the oxygen concentration is varied.

It is a matter of course that the invention is not limited to the above-described embodiment, and includes various modifications and equivalents falling within the spirit and scope of the claims appended hereto.

For example, the embodiment, the microcomputer 60 disposed in the controller 300 calculates the NO concentration and the $NO_2$ ratio, and supplies the calculated $NO_2$ ratio to a deterioration determining unit 221 in the ECU 220. The invention is not limited thereto. A NO concentration calculating unit may be disposed in the ECU 220, the $NO_2$ and $NO_x$ concentrations which are calculated by the microcomputer 60, and which are obtained after correction of the $O_2$ concentration may be supplied to the NO concentration calculating unit in the ECU 220, and the NO concentration and the $NO_2$ ratio may be calculated in the ECU 220. Alternatively, a NO concentration calculating unit may be disposed in the ECU 220, the NO concentration may be calculated by the microcomputer 60, the NO concentration may be then supplied to the NO concentration calculating unit in the ECU 220, and the $NO_2$ ratio may be calculated in the ECU 220.

Figure 9:
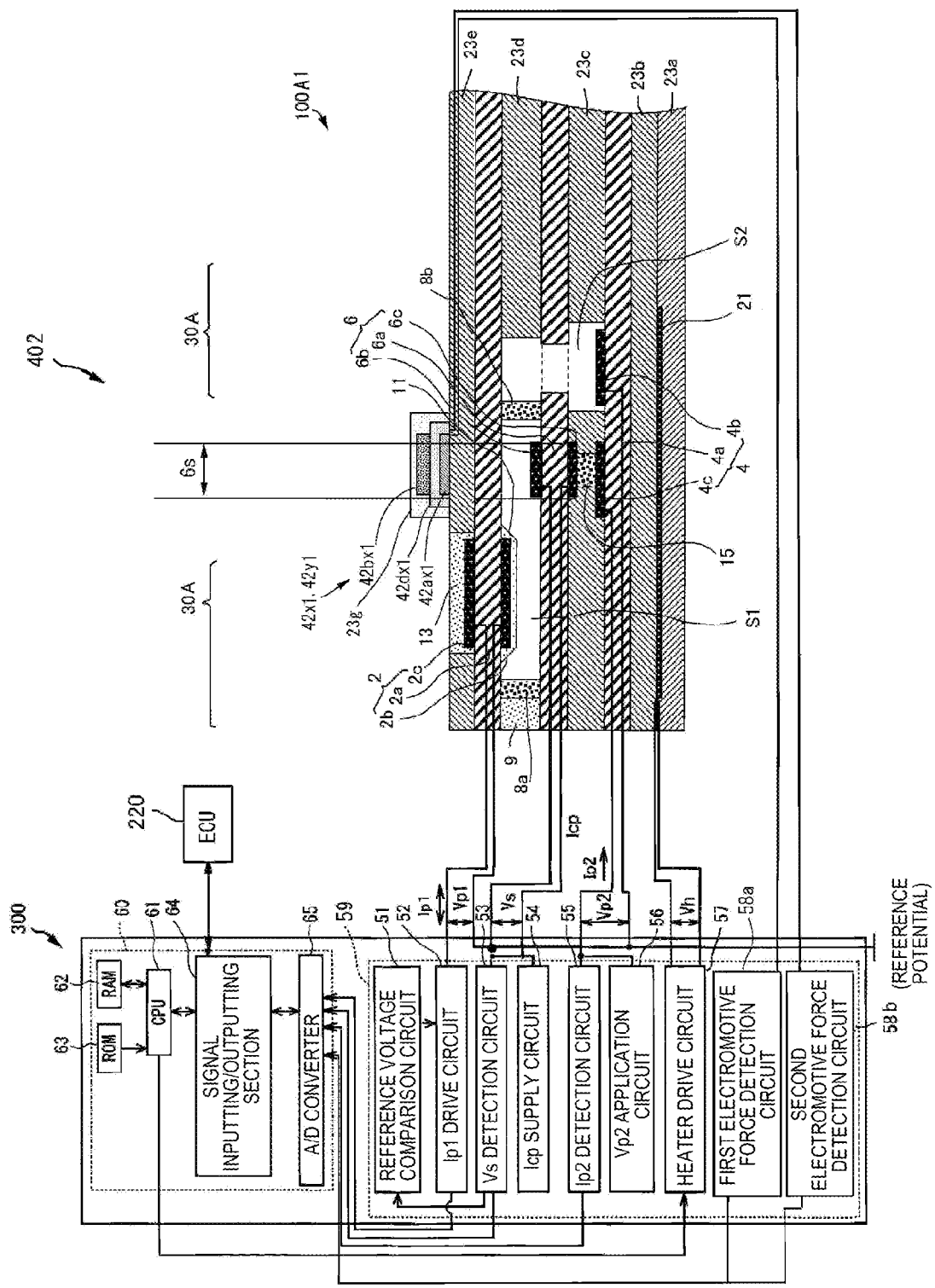
FIG. 9 is a block diagram showing other configurations of the multigas sensor and the gas sensor controller.

In the embodiment, the ammonia sensor portions 42x, 42y are disposed on the surface of the insulation layer 23a. The invention is not limited thereto. As shown in FIG. 9, for example, ammonia sensor portions 42x1, 42y1 may be disposed on the surface of the insulation layer 23e which is the outer surface (upper surface) of the $NO_x$ sensor portion 30A. In this case, however, also the ammonia sensor portions 42x1, 42y1 disposed on the surface of the insulation layer 23e are placed so as to overlap with at least the first region 6s of the oxygen concentration detection cell 6. The multigas sensor device 402 shown in FIG. 9 is identical with the multigas sensor device 400 of FIG. 2 except the positions of the ammonia sensor portions 42x1, 42y1 and the configuration of a multigas sensor element portion 100A1. Therefore, components identical with those of the multigas sensor device 400 are denoted by the same reference numerals, and their description is omitted.

The positional relationships between the first and second ammonia sensor portions and the oxygen concentration detection cell 6 are not limited to those in the embodiment.

Figure 10:
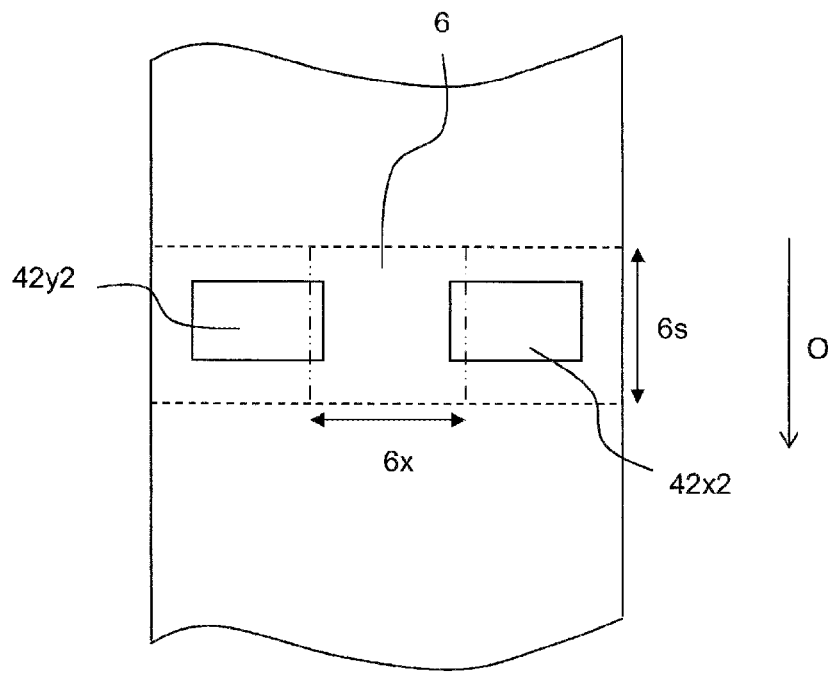
FIG. 10 is a plan view showing other positional relationships of the first and second ammonia sensor portions and the oxygen concentration detecting cell.

As shown in FIG. 10, for example, first and second ammonia sensor portions 42x2, 42y2 may be positioned on both sides in the width direction across the second region 6x, and overlap with the second region 6x. Also in the embodiment of FIG. 10, both the ammonia sensor portions 42x2, 42y2 are adjacent to the oxygen concentration detection cell 6. As compared with the case where the ammonia sensor portions 42x2, 42y2 are placed on one side of the oxygen concentration detection cell 6, and only one of the ammonia sensor portions is adjacent to the oxygen concentration detection cell 6, therefore, the temperature difference between the ammonia sensor portions 42x2, 42y2 can be suppressed, and the temperature dependency of the sensitivity ratios can be further reduced.

Figure 11:
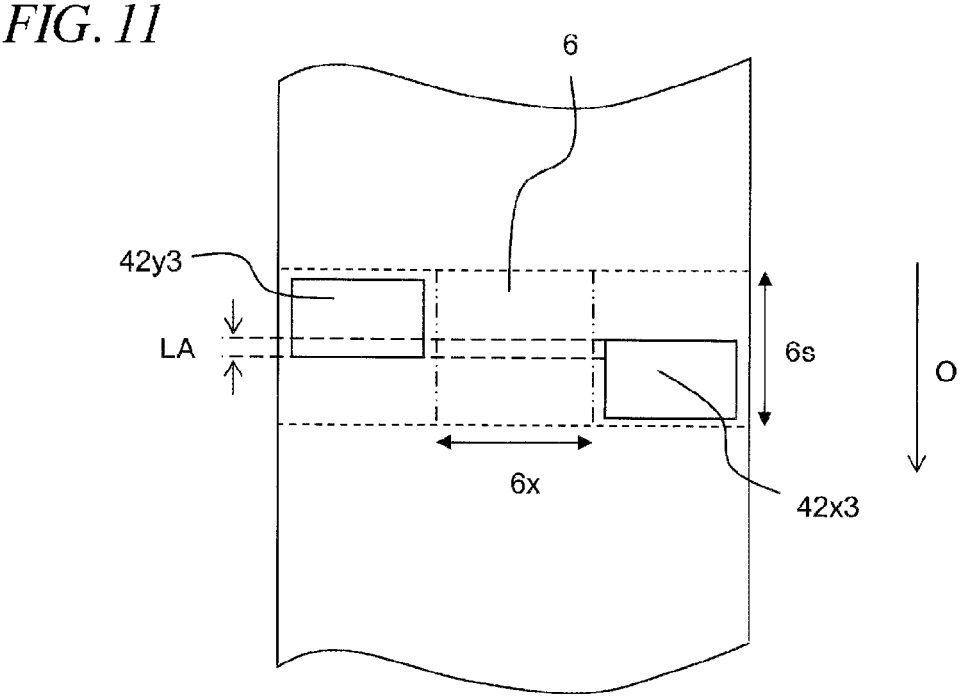
FIG. 11 is a plan view showing further positional relationships of the first and second ammonia sensor portions and the oxygen concentration detecting cell.

As shown in FIG. 11, in first and second ammonia sensor portions 42x3, 42y3, partial regions LA may overlap with each other in the first region 6s in the axial direction. In the embodiment of FIG. 11, since the heater has a heating portion and lead portions in the axial direction, the heater generates heat unevenly in the axial direction. The first and second ammonia sensor portions 423x, 42y3 partly overlap each other in the regions LA in the axial direction. In the overlapping portion (the region LA), therefore, the ammonia sensor portions 42x3, 42y3 are heated evenly by the heater in the axial direction. Consequently, the temperature dependency of the sensitivity ratios can be further reduced.

In the embodiments of FIGS. 10 and 11, the axial lengths of the first and second ammonia sensor portions 42x2 (42x3), 42y2 (42y3) are shorter than the axial length of the first region 6s, and the ammonia sensor portions 42x2, 42y2 (42x3, 42y3) are located inside the first region 6s in the axial direction.

Figure 12:
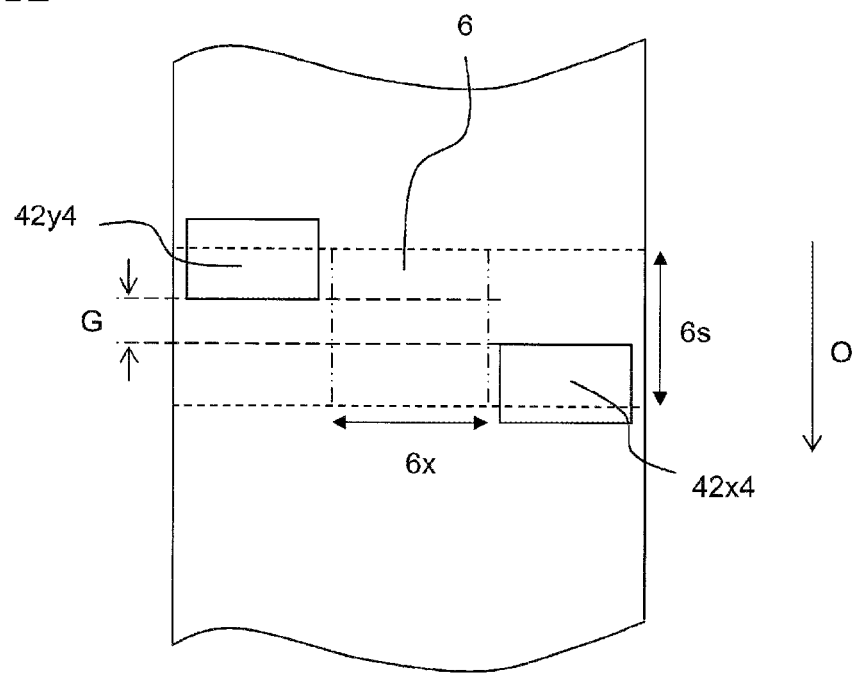
FIG. 12 is a plan view showing yet further positional relationships of the first and second ammonia sensor portions and the oxygen concentration detecting cell.

As shown in FIG. 12, the first and second ammonia sensor portions 42x4, 42y4 may not overlap with each other in the first region 6s in the axial direction, and may be separated from each other by a region G. Also in the embodiment of FIG. 12, at least parts of the first and second ammonia sensor portions 42x4, 42y4 overlap with the first region 6s, and hence the ammonia sensor portions 42x4, 42y4 are positioned in the first region 6s which is in the vicinity of the oxygen concentration detection cell 6. Therefore, the temperatures of the ammonia sensor portions 42x4, 42y4 are stabilized, and an effect of reducing the temperature dependency of the sensitivity ratios themselves is reduced is achieved. In the embodiment of FIG. 12, the front end side of the first ammonia sensor portion 42x4 protrudes from the first region 6s toward the front end, and the rear end side of the second ammonia sensor portion 42y4 protrudes from the first region 6s toward the rear end.

Figure 13:
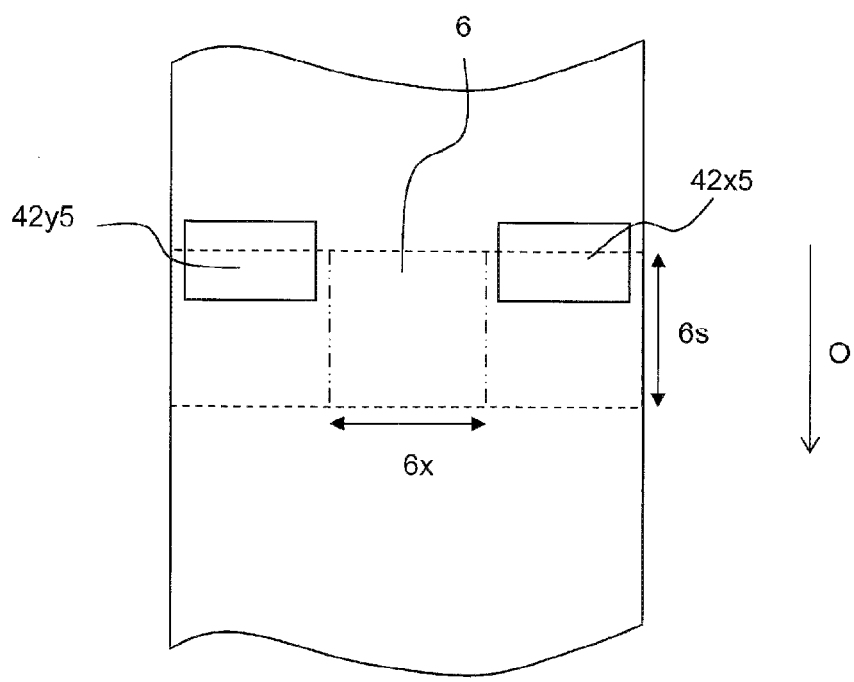
FIG. 13 is a plan view showing yet further positional relationships of the first and second ammonia sensor portions and the oxygen concentration detecting cell.

As shown in FIG. 13, first and second ammonia sensor portions 42x5, 42y5 may be positioned on the same side in the axial direction in the first region 6s (in the example of FIG. 13, the ammonia sensor portions 42x5, 42y5 are on the upper side of the first region 6s). Also in the embodiment of FIG. 13, at least parts of the first and second ammonia sensor portions 42x5, 42y5 overlap with the first region 6s, and hence the ammonia sensor portions 42x5, 42y5 are positioned in the first region 6s which is in the vicinity of the oxygen concentration detection cell 6. Therefore, the temperatures of the ammonia sensor portions 42x5, 42y5 are stabilized, and an effect of reducing the temperature dependencies of the sensitivity ratios themselves is achieved. In the embodiment of FIG. 13, the rear end sides of the first and second ammonia sensor portions 42x5, 42y5 protrude from the first region 6s toward the rear end.

In the embodiments of FIGS. 12 and 13, the first and second ammonia sensor portions 42x4 (42x5), 42y4 (42y5) are positioned on both sides in the width direction across the second region 6x.

Figure 14:
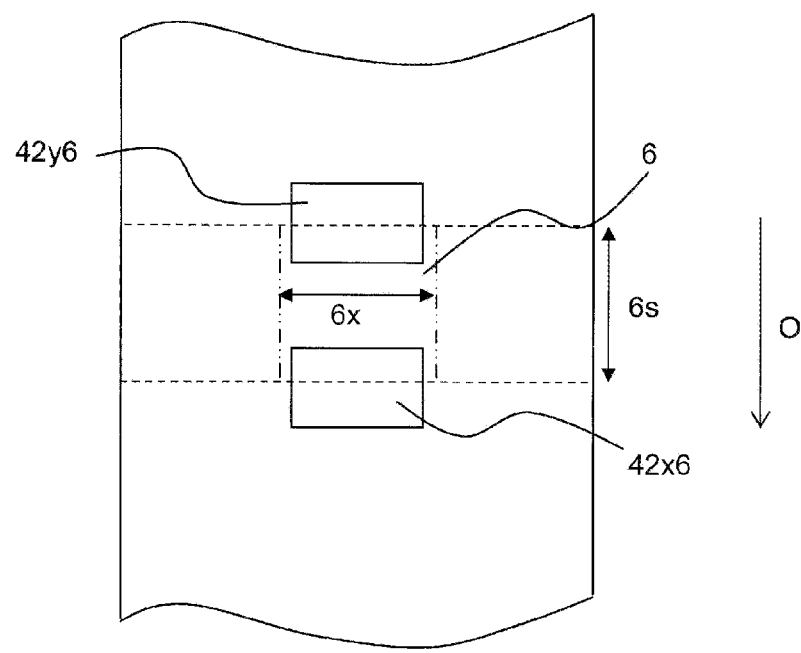
FIG. 14 is a plan view showing yet further positional relationships of the first and second ammonia sensor portions and the oxygen concentration detecting cell.

As shown in FIG. 14, first and second ammonia sensor portions 42x6, 42y6 may be positioned in the second region 6x, and may be separated from each other in the first region 6s without overlapping in the axial direction. Also in the embodiment of FIG. 14, at least parts of the first and second ammonia sensor portions 42x6, 42y6 overlap with the first region 6s, and hence the ammonia sensor portions 42x6, 42y6 are positioned in the first region 6s which is in the vicinity of the oxygen concentration detection cell 6. Therefore, the temperatures of the ammonia sensor portions 42x6, 42y6 are stabilized, and an effect of reducing the temperature dependency of the sensitivity ratios is achieved.

In the embodiment of FIG. 14, the front end side of the first ammonia sensor portion 42x6 protrudes from the first region 6s toward the front end, and the rear end side of the second ammonia sensor portion 42y6 protrudes from the first region 6s toward the rear end.

The invention has been described in detail with reference to the above embodiments. However, the invention should not be construed as being limited thereto. It should further be apparent to those skilled in the art that various changes in form and detail of the invention as shown and described above may be made. It is intended that such changes be included within the spirit and scope of the claims appended hereto.

This application is based on Japanese Patent Application No. 2013-143263 filed Jul. 9, 2013 and Japanese Patent Application No. 2014-109777 filed May 28, 2014, incorporated herein by reference in their entirety.

What is claimed is:

1. A multigas sensor which comprises:
   a multigas sensor element portion including:
   a $NO_x$ sensor portion which detects a concentration of $NO_x$ in a gas to be measured; and
   two ammonia sensor portions which detect a concentration of ammonia in the gas to be measured, the sensor portions being first and second ammonia sensor portions having different ratios between a sensitivity of ammonia and a sensitivity of $NO_x$,
   wherein the multigas sensor element portion has a plate shape which extends in an axial direction, a temperature detecting portion which controls a temperature of the $NO_x$ sensor portion is disposed in the multigas sensor element portion, and the first and second ammonia sensor portions are disposed on an outer surface of the $NO_x$ sensor portion, at least parts of the first and second ammonia sensor portions overlapping with a first region of the multigas sensor element portion, the first region being defined in a width direction by ends in the axial direction of the temperature detecting portion.

2. The multigas sensor as claimed in claim 1, wherein all parts of the first and second ammonia sensor portions overlap the first region.

3. The multigas sensor as claimed in claim 1, wherein the temperature detecting portion is positioned in a middle portion in the width direction of the multigas sensor element portion, and the first and second ammonia sensor portions are disposed on both sides in the width direction of the first region across a second region which is defined in the axial direction by ends in the width direction of the temperature detecting portion.

4. The multigas sensor as claimed in claim 3, wherein the first and second ammonia sensor portions are positioned so as to be shifted away from the second region.

5. The multigas sensor as claimed in claim 1, wherein the $NO_x$ sensor portion is configured by stacking a $NO_x$ sensing portion in which the temperature detecting portion is disposed and a heater for heating the $NO_x$ sensing portion, and the first and second ammonia sensor portions are disposed on an outer surface of the $NO_x$ sensor portion on a side of the heater in a stacking direction of the multigas sensor element portion.

6. The multigas sensor as claimed in claim 1, wherein the $NO_x$ sensor portion is configured by stacking a $NO_x$ sensing portion in which the temperature detecting portion is disposed and a heater for heating the $NO_x$ sensing portion, the heater has a heating portion on a front end side of the heater in the axial direction and a pair of lead portions that extends from the heating portion toward a rear end in the axial direction, and the first and second ammonia sensor portions at least partly overlap each other in the axial direction in the first region.

7. The multigas sensor as claimed in claim 6, wherein all parts of one of the first and second ammonia sensor portions overlap with another one of the first and second ammonia sensor portions in the axial direction in the first region.

8. The multigas sensor as claimed in claim 6, wherein each of the first and second ammonia sensor portions includes a solid electrolyte body and a pair of electrodes which are disposed respectively on opposing surfaces of the solid electrolyte body, and one of the paired electrodes is disposed on the outer surface of the $NO_x$ sensor portion.

9. The multigas sensor as claimed in claim 1, wherein axial lengths of the first and second ammonia sensor portions are shorter than an axial length of the first region.

10. The multigas sensor as claimed in claim 1, wherein a protective layer which covers the first and second ammonia sensor portions is disposed in the multigas sensor, and the protective layer integrally covers both the first and second ammonia sensor portions.

11. A multigas sensor device, comprising:
the multigas sensor as claimed in claim 1; and
a calculating portion which calculates concentrations of nitrogen monoxide, nitrogen dioxide, and ammonia contained in the gas to be measured, based on outputs of the $NO_x$ sensor portion, the first and second ammonia sensor portions.

* * * * *